(12) United States Patent
Yoon

(10) Patent No.: US 7,171,862 B2
(45) Date of Patent: Feb. 6, 2007

(54) PACKAGE BIOCHEMICAL HAZARD AND CONTRABAND DETECTOR

(76) Inventor: Sung Hoon Yoon, 218 Broad Ave. Apt. 3C, Leonia, NJ (US) 07605

( * ) Notice: Subject to any disclaimer, the term of this patent is extended or adjusted under 35 U.S.C. 154(b) by 0 days.

(21) Appl. No.: 11/301,548

(22) Filed: Dec. 13, 2005

(65) Prior Publication Data

US 2006/0213253 A1     Sep. 28, 2006

Related U.S. Application Data

(63) Continuation of application No. 10/281,680, filed on Oct. 28, 2002, now Pat. No. 7,032,467.

(60) Provisional application No. 60/344,635, filed on Oct. 26, 2001.

(51) Int. Cl.
*G01N 1/38* (2006.01)

(52) U.S. Cl. .................... 73/863.81; 73/23.2; 73/24.01; 73/24.06; 73/31.03; 73/864.33

(58) Field of Classification Search ................ 73/23.2, 73/24.01, 24.06, 31.03, 31.07, 863.81, 864.33, 73/31.05

See application file for complete search history.

(56) References Cited

U.S. PATENT DOCUMENTS 4,580,440 A * 4/1986 Reid et al. ................. 73/31.07
5,942,699 A * 8/1999 Ornath et al. ............ 73/863.21

* cited by examiner

*Primary Examiner*—Daniel S. Larkin
(74) *Attorney, Agent, or Firm*—Law Offices of Rita C. Chipperson, P.C.; Rita C. Chipperson

(57) ABSTRACT

The disclosed apparatus and methods allow collection of concentrated samples of content in shipping packages without unsealing the package by forcing airflow via existing hidden gaps or, if necessary, creating one by a small incision. The air is injected into the hidden gaps by either probe or socket device to disturb and agitate contents inside the package, causing the contents to loosen and blending particulates on the surface into the air stream. Airborne particles are channeled into a detection device, where the particulates are concentrated. Display and warning apparatus receive and record the analysis results from the detection device. If the analysis finds that predetermined selection and sensitivity criteria for target hazard or contraband material are met, then the warning apparatus initiates the appropriate alert protocols.

23 Claims, 4 Drawing Sheets

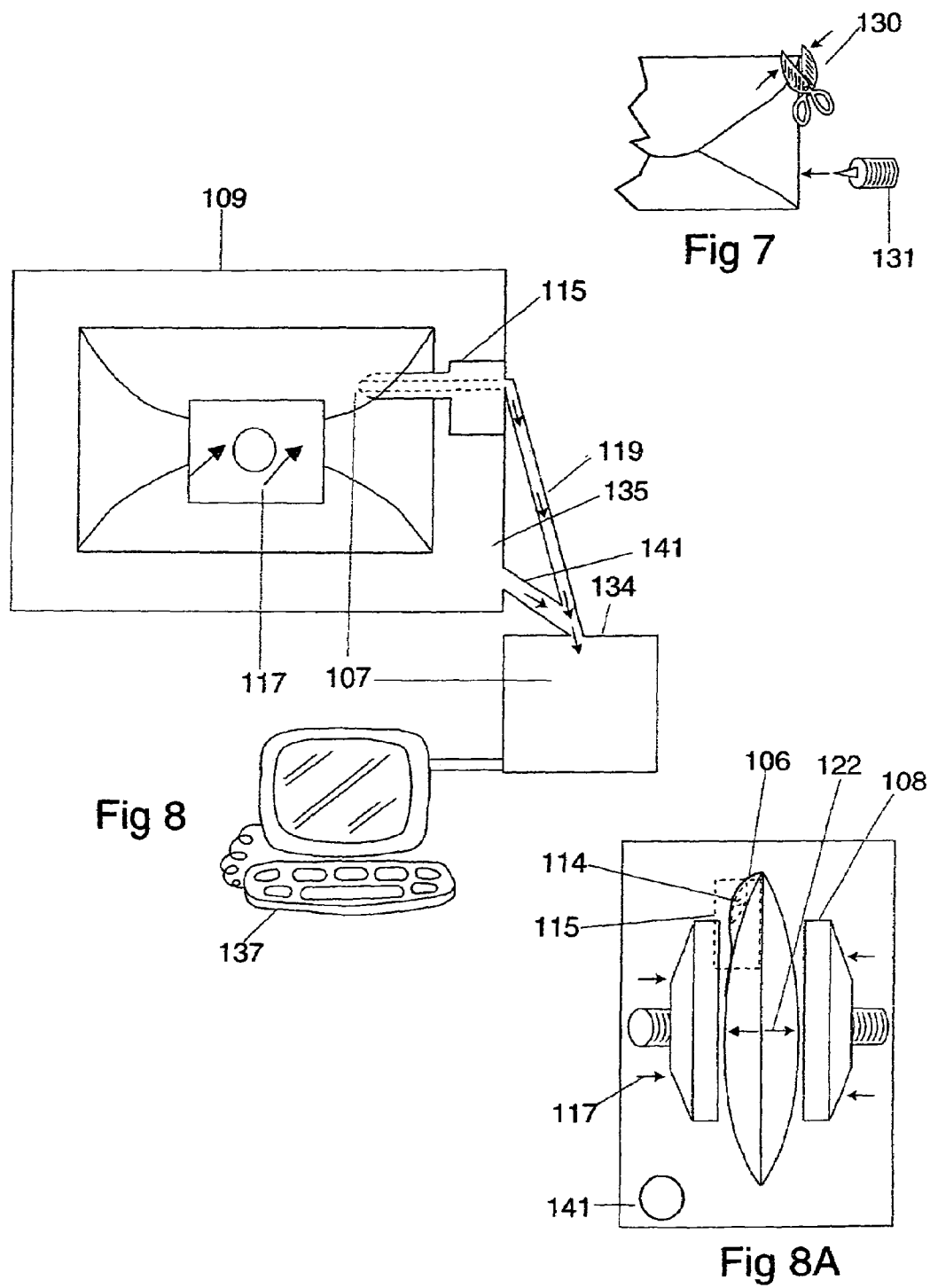

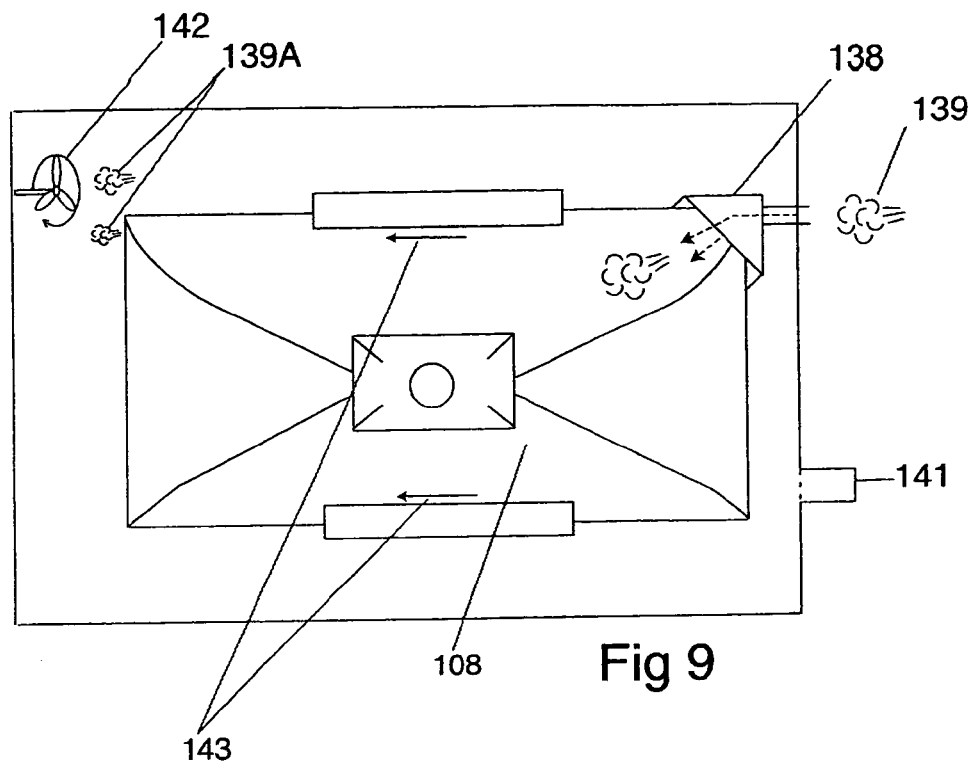
Fig 9
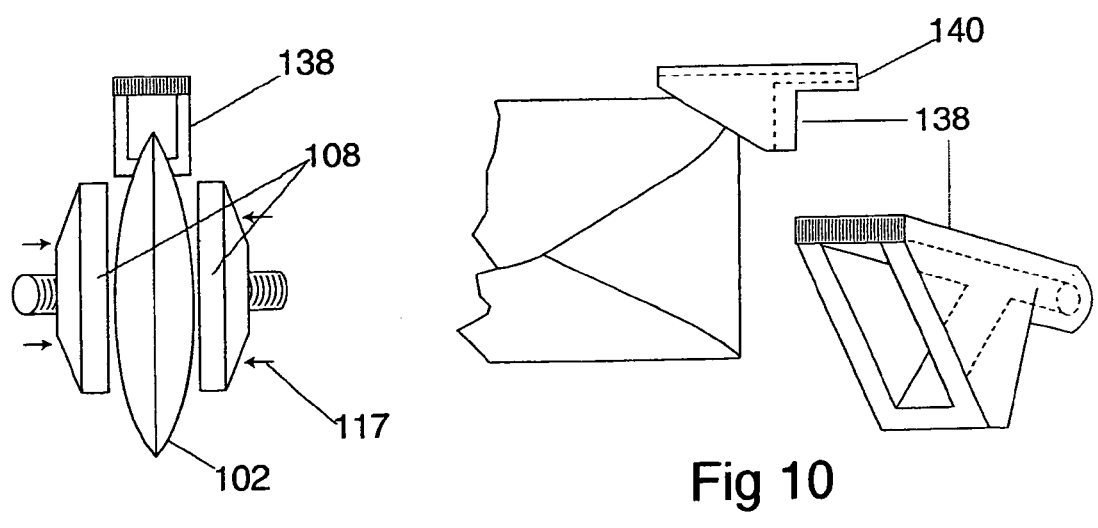
Fig 9A
Fig 10

PACKAGE BIOCHEMICAL HAZARD AND CONTRABAND DETECTOR

CROSS-REFERENCE TO RELATED APPLICATIONS

This patent application is a continuation of U.S. patent application Ser. No. 10/281,680, now U.S. Pat. No. 7,032,467, entitled "Package Biochemical Hazard and Contraband Detector" filed on Oct. 28, 2002, which is incorporated herein by reference. This application also claims the benefit of U.S. Provisional Application Ser. No. 60/344,635, entitled "Biological and Chemical Hazard (BACH) Package Tester" filed on Oct. 26, 2001.

BACKGROUND OF THE INVENTION

The following relates to apparatus and method to detect hazardous or illegal contraband hidden within shipping, delivery, mail, or postal packages for analysis and defense without fully unsealing the packages by probing the interior with airflow and collecting concentrated sample particles.

According to the US Department of Justice guide (NIJ Guide 101-00), most of the well known biological weapon agents such as, anthrax, Brucellosis, Tularemia, Cholera, Glanders, Melioidosis, Plague, Marburg Virus, Smallpox Virus, Venezuelan Equine Encephalitis, Ebola Virus, Q Fever, Botulinum Toxin, Staphylococcal enterotoxin B, Tricothecene mycotoxins, and Ricin could take aerosol form. The agency further states, "The primary infection route from exposure to biological agents is through inhalation".

During the year 2001, envelopes containing anthrax spores were sent via the US Postal Service. The cutaneous form of anthrax spores caused havoc as it infected people who came in direct contact with the hazardous powder. However, the inhalation form of anthrax spores caused even greater fear and devastation, as the fine airborne spores randomly contaminated nearby packages and killed indiscriminately and capriciously. Moreover, the inhalation form was much deadlier than the cutaneous form, as many died even with antibiotic treatments.

Soon afterward, the fear of other biological agents and envelopes containing non-toxic materials preyed on the fear. Although no one suffered illness or death, the flood of "hoax-envelopes" was nearly as effective in terrorizing the public and consuming valuable resources as the real biological attacks, as every incident had to be treated like the real thing.

In response, the US Government irradiated mail packages bound for various government agencies and certain targeted private sectors. Even after a three billion dollar budget was allotted and nearly a year had passed since the incidents, the majority of the mail packages sent to the general public have yet to be irradiated or otherwise protected.

Some reasons for this are that irradiation is an expensive process, it takes a long time to implement, and it alone cannot pinpoint the contaminated or hoax mail. Additionally, the possibility of infection among those unfortunate postal workers prior to irradiation at a central processing unit can be tragic. Also, the irradiated mail may cause health problems for the recipients. Many congressional workers had complained of headache, nose bleeding, diarrhea, and other ailments. As a result, many members of the public oppose and fear the irradiation process.

In addition, the irradiated mail must be stored for several days to lower the level of radiation, which delays delivery and incurs storage costs. Also, no clear procedure exists to avoid irradiating products such as electronic devices, film, glass and food items that can be damaged, destroyed, or even made harmful if they are exposed to massive doses of radiation.

Furthermore, exposing metal to ionizing radiation can induce radioactivity if enough of it collects on the surfaces. The mail includes a large quantity of metal in the form of binders, paperclips, and pens, not to mention all of the consumer products containing metal that are routinely shipped via the U.S. Postal Service, that could cause such an exposure. Additionally, irradiation requires nuclear materials to keep it operating. Transporting radioactive material, improper worker safety, and environmental contamination from leaks, spills, and mishaps of radioactive material can lead to disasters. Yet another concern is that a terrorist may attack the irradiation facility, transport, or storage to obtain the irradiated material to create a "dirty bomb".

In summary, the effectiveness of the irradiation process may be exaggerated. A New Jersey official described some of the challenges in a memo. "After much discussion about the penetration of the electron beam," she wrote, "it was determined that the package would have to be turned over and run through irradiator a second time. The problem is that the spores in the envelopes would presumably fall to the bottom by gravity, thus avoiding the beam for both passes."

Another patent pending idea by Gary Mize called "Biosafe Mailbox" uses time released toxins like chlorine dioxide or methyl bromide in a mailbox prior to pick up. This idea also suffers from many of the problems associated with irradiation. The toxins that are used to destroy the biological agents are themselves dangerous chemicals, are probably only effective against a limited quantity of biological agents, and are ineffective against chemical toxic agents. Moreover, reconfiguring every mailbox to release and recycle these chemicals could be not only very expensive, but also potentially harmful, as toxins may be released into the environment. Furthermore, these processes can be thwarted easily using lead foils to block the irradiation. Airtight packaging can also stop the decontaminants.

The danger to the public when using a mail delivery service, however, is not new. Long before biochemical terrorism, illegal contrabands such as bombs, poisons, illegal drugs, and the like have been sent using the US Postal Service.

Also, available technologies like Ion Mobility Spectrometry (IMS), vapor detection, gas chromatograph, reactive chemicals, and similar processes have had only limited use for detecting hazards and contraband inside delivery packages because collecting concentrated content samples from a sealed container proves to be difficult.

X-ray and swab collection methods, often used in airports, would be ineffective, too costly, and too time consuming to use for delivery services due to high volumes. Tens of millions of letters and packages that are sent by delivery services per day cannot be individually viewed and swabbed.

A better sample collection and concentration apparatus and method must be utilized, if advanced analytic technologies are to be implemented.

BRIEF SUMMARY OF THE INVENTION

Whether it is real or a hoax, the best defense against bio-terrorists or other criminal activities, is catching and prosecuting the perpetrator. To catch the offenders, law enforcement must be able to identify the crime quickly and secure the evidence without destroying or altering it. As selection, detection, and identification technologies improve, such as nucleic acid amplification or antibody binding methods, obtaining enough concentrated sample, quickly cueing the existence of the possible target agents inside the package, and preserving the evidence becomes critical.

The idea described herein is an inexpensive and effective apparatus and method to collect concentrated possible biochemical hazard and other illegal contraband samples in packages for analysis. Given that the envelope has been the choice vehicle of delivery by the terrorists and many other illegal activities, an envelope will be used as an example, however other shipping packages can also utilize similar apparatuses and methods.

Most shipping or mail packages are semi-sealed and have gaps or openings where packaging material edges meet. This is to prevent air from being trapped inside the package and turning it into a balloon, because a ballooned envelope takes up excess space and causes problems when transporting. Shipping or mailing packages usually do not contain particles that resemble the size and weight of biological pathogens or chemical toxins and bombs and illegal drugs exhibit specific particle characteristic signatures. The possible harmful particles in the packages are of such size and weight that they should become airborne and mobile by introducing air or gas flow via the gap.

In summary, the process results in the following objectives and advantages: provides a cheap and effective apparatus to thwart biochemical terrorism rather than using expensive and dangerous ultraviolet sterilization methods, slow x-ray processes, or expensive new mailboxes without unsealing the package, provides safe and easy operation, as the process does not require dangerous radiation or chemicals, provides a method to help quickly apprehend criminals and reduce exposure, because the method could detect the presence of foreign particles early and stop it from going to the addressee or another transfer agent, provides a defense against hoax biological terror attacks, provides a better and more concentrated sample collection, and provides additional testing for many illegal contrabands like illegal drugs and bombs.

In accordance with the present invention, disclosed is a simple, safe, and effective concentrated sample collection and cueing apparatus and method for use against biochemical hazard and illegal contrabands which does not require fully unsealing shipping, delivery, mail, or postal packages.

Further objects and advantages will become apparent from a consideration of the drawings and ensuing description.

BRIEF DESCRIPTION OF THE SEVERAL VIEWS OF THE DRAWINGS

FIG. 7 depicts the envelope being infiltrated by a pair of scissors or a syringe.

FIG. 8 depicts the airtight box in FIG. 3 attached to a detection device and a warning system.

FIG. 8A shows a side view of the airtight box with an inflated envelope in the middle of the side compressor clamp with sensors.

FIG. 9 depicts a frontal view with a socket lip device variant to the probe used in FIG. 4.

FIG. 9A depicts a side view of FIG. 9.

FIG. 10 shows the socket lip device of FIG. 9 in detail.

REFERENCE NUMERALS IN DRAWINGS

Figure 1:
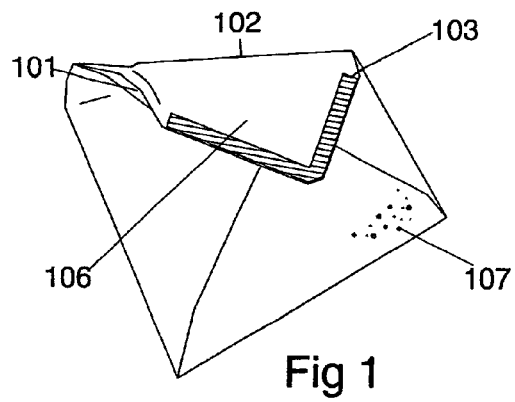
FIG. 1 depicts a standard sealed US envelope with a small gap or opening highlighted.

101. Hidden gap or opening in mailing package
102. Envelope
103. Envelope adhesive area
105. Express Mail shipping package
106. Envelope Flap
107. Possible biochemical hazard material (inside the envelope)
108. Side compressor clamp pairs connected to sensors for checking inflation of the envelope
109. Airtight container or box in this embodiment
110. Airtight box door
111. Conveyer system (to deliver the envelope to the box)
112. Mechanical clamp pairs (to hold the envelope in place)
114. Mechanical probe
114A. Straight probe
114B. Narrow probe
114C. Bent Probe
114D. Slanted Probe
114E. Hollow channel running down the middle of the probe
115. Probe control box
116. Probe movements from rest to under the envelope flap
117. Side clamp movements (coming together to squeeze the envelope)
118. Tube to pump air or gas into the envelope
119. Tube for vacuuming out the air or gas
122. Inflation or ballooning of envelope sidewalls by air
123. A rod guide for the probe control box movement
124. Lowering motion of the control box along the rod guide
125. Axis to turn the box
126. The airtight box rotating around the axis
130. Mechanical scissor (cutting motion)
131. Syringe-like device (punching a hole)
133. Forced movement of air or gas
134. Detection or analytic device (for concentration and analysis of particulates)
135. Possible biochemical hazard material airborne
137. Display and warning apparatus
138. Socket lips device
139. Airflow into the envelope socket lips device above
139A. Residual airflow
140. Hole connected tube to force air into envelope via the socket device
141. Hole in the box with vacuum tube to collect sample particles
142. Airflow measurement device
143. Backward pressure on the clamp

DETAILED DESCRIPTION OF THE INVENTION

Figure 2:
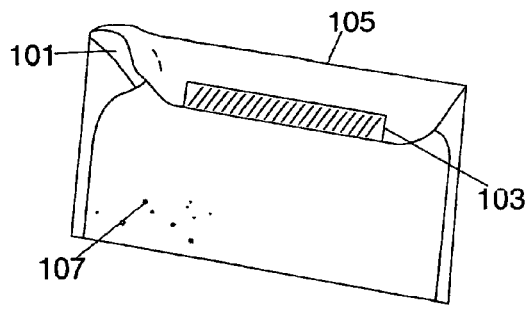
FIG. 2 depicts a sealed express mail package also with a gap highlighted.

As depicted in FIG. 1 and FIG. 2, the vast majority of envelopes or packages used in the US have small gaps or openings on the top corners where edges come together that can be probed without unsealing the subject. Opening 101 still exists even when flap 106 on envelope 102 or package 105 is closed and sealed.

In FIG. 2, an adhesive area 103 does not extend all the way out to the corner edge of the envelope. This creates the gap above, which exists to vent air in and out when being handled. Without it, the envelope will not flatten as trapped air creates ballooning, which will then cause problems as it travels through the processing plants. The small opening is well concealed and covered by the flap. This cover usually keeps possible hazardous and contraband particles 107 trapped inside the envelope.

Figure 3:
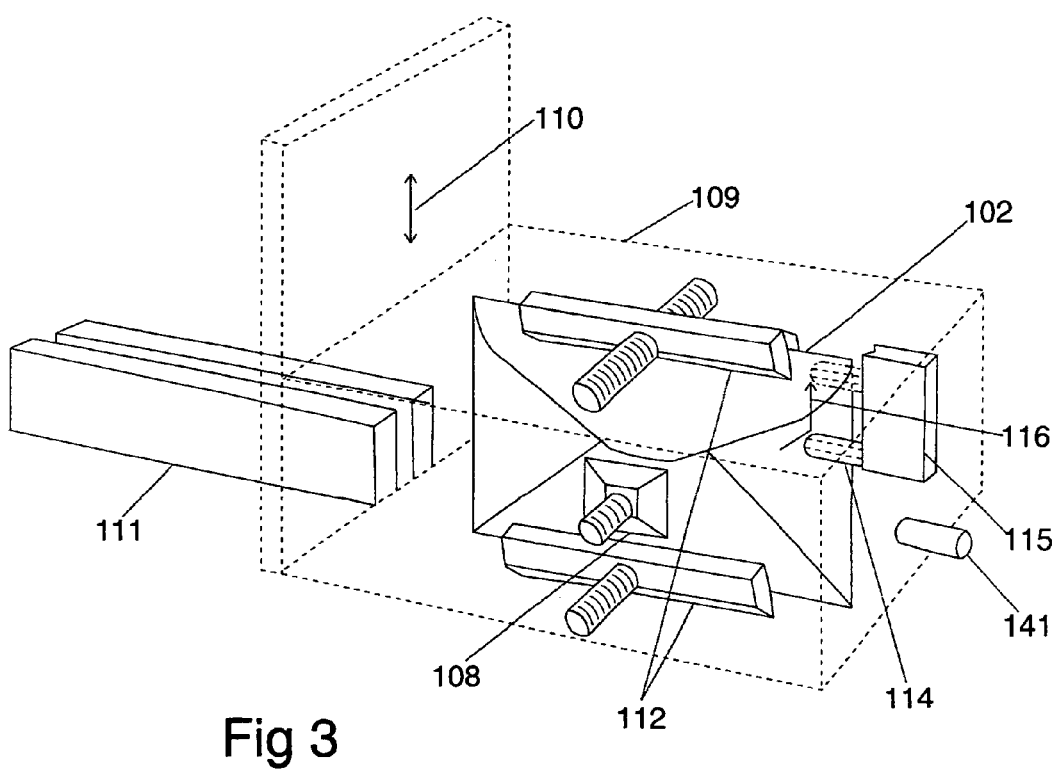
FIG. 3 depicts an airtight container with the above envelope inserted with clamps, sensors, and probe control box.

As shown in FIG. 3, the envelope 102 travels by conveyer belt mechanism 111 or gloved human hands to an airtight container 109, which is a box in this embodiment. Once inside the airtight box, envelope 102 is secured by holding clamps 112 on an outer edge of the envelope sides. In this embodiment, top and bottom clamps are utilized. The envelope is locked in the box by closing airtight door 110. Once envelope 102 has been secured by the operations just described, side compressor clamps 108 may be moved, with optical or pressure sensors (not shown), close against the side walls of the envelope such that, when the envelope is inflated, the ballooning envelope sidewalls push back the side clamps. FIG. 3 also illustrates the probe attached to control box 115 at rest prior to exploring the gap. By using optical or mechanical sensors, small probe 114 may be mechanically slid under the envelope flap by following arrow movements 116. This operation is described in further detail below.

Figure 4:
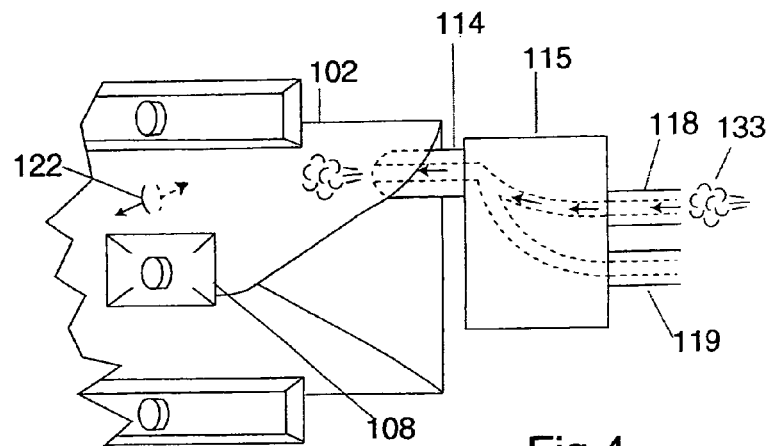
FIG. 4 depicts the frontal right half view of the inserted and clamped secure envelope from FIG. 3.

FIG. 4 shows the exposed front right half of the airtight box from FIG. 3 in detail with some items inside mechanical control and sensor box 115 with attached probe. The control box contains mechanical devices with sensors (not shown) to guide probe 114 underneath envelope flap 106. The exact mechanical and sensor devices to guide the probe into the gap are not included as part of the invention. The control box contains two air hoses inside. First hose 118 injects the air or gas to the probe tip and inflates 122 the envelope during the insertion process show in movement 116. Second hose 119 will be then used later for collecting a sample by vacuuming the air and particles inside the envelope after ballooning, as shown in FIGS. 8 and 8A.

Figure 4A:
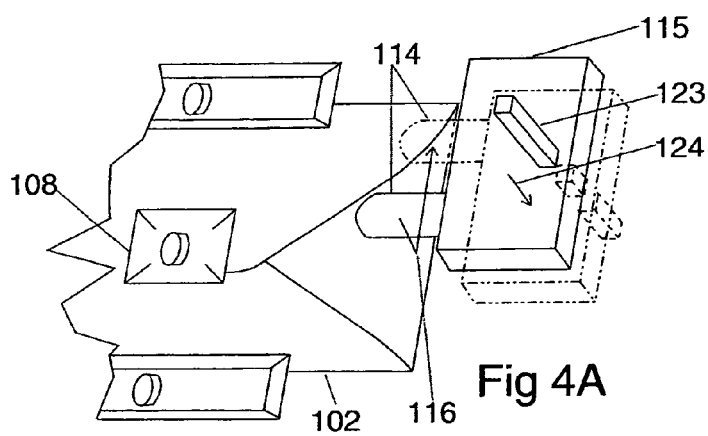
FIG. 4A depicts a perspective view of FIG. 4 to illustrate the probe and control box in more detail.

FIG. 4A shows a detailed perspective view of FIG. 4 with one embodiment of the probe and the control box movement. The probe is attached to control box 115, which is attached to guiding rod 123. The control box apparatus is lowered and rested along guide rod 123 on top of the envelope and inserted under the flap by mechanically traveling along the side of the envelope. As the probe slides up and approaches the flap, the probe expels a constant air stream from its tip to push the envelope wall and the flap further apart to enlarge the gap.

Figure 5:
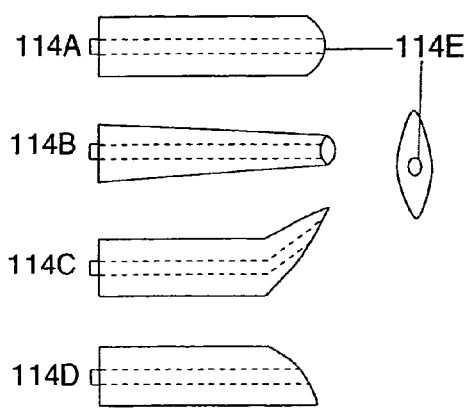
FIG. 5 depicts variations of probe shapes.

FIG. 5 is a closer look at variants of a probe. The probe can be varied like a straight tip 114A, a narrowed tip 114B, a bent tip 114C, or a slanted tip 114D. However, regardless of the exact shape or material, the probe is thin, dull, pointed, and a hollow device that can easily be slipped into the gap. Materials of the probe can be metal, ceramic, plastic, or the like. The outer shape of the probe may resemble the end of a letter opener knife, but a hollowed middle channel 114E extends from the tip to the end, which enables the air or gas movement back and forth from control box 115.

Figure 6:
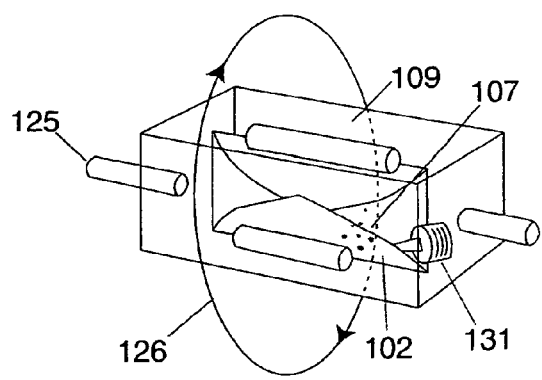
FIG. 6 depicts a bottom view of the airtight box in FIG. 3.

FIG. 6 shows an optional embodiment of the airtight box in FIG. 3 inverted to show possible rotation of the whole box apparatus in FIG. 3. The whole airtight box may be mechanically rotated 126 on axis 125 by turning on a motor (not shown) attached to the axis. As the box turns, gravity and centrifugal force will help to loosen the particles. Additionally, other motions like shaking or vibrating could achieve similar results. This step may be performed on the probed and ballooned envelope.

If the envelope fails to balloon by flowing air from the probe tip, a small opening may be cut with a pair of scissors 130 or a hole may be poked with a syringe 131 to create an opening that can be used to introduce air or gas inside the envelope, as seen in FIG. 7.

As in FIG. 8A, a determination may be made as to whether the gas has successfully penetrated the interior of the envelope and expanded envelope sidewalls 112 by checking the pressure exerted against the side clamp 108. Afterward, the envelope may be forced to deflate to induce the air/gas out of the envelope carrying the possible hazardous material by squeezing envelope walls together on both sides with the side clamps 117.

Turning to FIG. 8, the airborne biochemical hazard particles sample 135 may be collected via probe channel 114E using vacuum hose 119 and hole 141 in the box. The sample may then be sent to detection device 134, which can be a laser analyzer, a photometer, an optical particle counter (OPC), a condensation particle counter (CPC), an optoelectronic sensor, or other particle, optical, biological, or chemical analysis method.

Afterward, display unit 137 shows analyzed and stored results. The unit can be a combination of computer or electronic devices. The exact technical specification of the unit is not a part of the invention. If certain selection and sensitivity criteria are reached in any one or more of criteria like particle count, particle mass, particle density, particle concentration, chemical reaction, generic response, or the like, then an alarm alerts the operator by sound, flashing screen, e-mail, and/or other communication methods.

In an alternative embodiment as shown in FIG. 9, instead of using the probe, a socket or lips device 138 could gently fit against the envelope corner. The air or gas 139 may then be blown into the envelope via the socket device's hollow channel 140. As in the above procedures, the inflation may then be checked as in FIG. 9A and then the envelope may be deflated by the side clamps as in FIG. 8A. As the side clamps compress against the envelope, vacuum tube opening 141 attached to the wall of the airtight box may be used to collect the airborne particles sample. Once collected, the same hazard detection and alert method described above in operation 10 and 11 may be implemented.

Another way to check for successful airflow injection is illustrated in FIG. 9; airflow meter 142 measures the flow of residual airflow 139A. The residual flow rate and amount should diminish as airflow penetrates the inside of the envelope. Also, the injected airflow should cause backward pressure 143 on the top and bottom clamps.

FIG. 10 shows a socket or lips device 138 in detail. It is termed a socket or lips device because the device's two front walls sandwich an envelope corner with opening 101 in the middle such as a socket or lips would hold on to an item by grasping two opposite walls on the target item.

Additionally, the particle sample can be collected into a sealed container by this device for further testing. Alternatively, the whole airtight box may be removed and sent into the lab for further testing.

Problems could arise from probing underneath the envelope flap. This may be against the law for the US Post Office; however, the addressee should not have a problem. Addressees can even open the envelope fully by incision and fully test the contents. So, a pair of scissors or a cutting device could be used to either partially or fully create an incision to perform the particle test.

Alternatively, to avoid probing underneath the flap, the air can be simply pumped out utilizing a hole with a vacuum hose attached 141 on the wall of the box by squeezing the existing air pockets already in the envelope with the side clamp without inflating it or the envelope sidewalls could be pulled apart to let the air in through the gap by grasping on the envelope sidewalls using vacuum suction or a light adhesive on the side compressor clamp 108 on the envelope side walls. This action creates air inflow to the envelope, just as air is drawn into an accordion by pulling its sides apart. Additionally, forcing gas 133 into the envelope interior can be a toxin to kill any hazardous particles that might be inside the envelope.

In summary, from the description above, a number of advantages of the disclosed biochemical tester and method become evident. The operation is quick and simple, the operation can be assured of success by checking the package inflation or flow rate of air, and the operation provides the capability to vent contagions from the package or to deliver toxins to kill the contaminant particles without unsealing the package.

Accordingly, the reader will see that the biochemical tester and accompanying method of this invention can detect the presence of possible hazardous materials and illegal contraband in a shipping container simply, easily, safely, and assuredly.

Furthermore, the testing apparatus and method have additional advantages by providing quick alert against both real or false hazardous particles, by providing effective detection not only against biological, but chemical contrabands, such as poison, bombs, and illegal drugs, by allowing preservation of the evidence for prosecution, by providing a verification method of successful operation via inflation of the package or measured airflow change, by allowing testing of the vast majority of shipment or mail packages, including most envelopes, express mail packages, envelopes with forwarding address hole opening, many box packages and the like, by providing an adaptable platform to launch future improved analytic devices and approaches, by allowing safe operation in detection only mode by using only air in a preferred embodiment rather than using toxins or irradiation, by allowing a much more effective and assured way to kill certain biological hazards via the verification process described above if a toxin is used rather than just air and, by allowing testing of packages in it original semi-sealed state.

Although the description above contains much specificity, these should not be construed as limiting the scope of the invention but as merely providing illustrations of some of the presently preferred embodiments of this invention.

For example, rather than checking for inflation of a package, which may have stiff and rigid walls, the slower flow rate and volume of air or pressure exerted on holding clamps can be used to check for infiltration of gas inside a package.

Thus, the scope of the invention should be determined by the appended claims and their legal equivalents, rather than by the examples given.

I claim:

1. An apparatus for detecting a biochemical hazard in a package comprising:

at least one of the group consisting of an airtight container and an approximately airtight container having a first end and a second end;

at least one opening operatively attached to said first end, wherein said at least one opening opens to receive a package and closes thereafter to return said at least one of the group consisting of said airtight container and said approximately airtight container to an airtight state or an approximately airtight state;

at least one clamping device located internal to said at least one of the group consisting of said airtight container and said approximately airtight container for holding said package upon receipt of said package in said at least one of the group consisting of said airtight container and said approximately airtight container;

at least one circulator, wherein at least a portion of said circulator is coupled to or located internal to said at least one of the group consisting of said airtight container and said approximately airtight container for disturbing particles located inside said package via circulation of at least one of the group consisting of air, gas, and combinations thereof by said circulator;

at least one collector coupled to said at least one of the group consisting of said airtight container and said approximately airtight container to receive particles from at least one of the group consisting of said airtight container, said approximately airtight container, said inside of said package, and combinations thereof; and at least one biochemical detector coupled to said collector to analyze said particles.

2. An apparatus according to claim 1, wherein said at least one of the group consisting of said airtight container and said approximately airtight container is a box.

3. An apparatus according to claim 1, wherein said at least one opening is a door.

4. An apparatus according to claim 1, wherein said at least one clamping device is at least one of the group consisting of a clamp, a clip, an adhesive, suction, tongs, forceps, pincers, nippers, pliers, a vice, and combinations thereof.

5. An apparatus according to claim 1, wherein said at least one circulator includes at least one of the group consisting of a probe, a socket device, a lip device, a fan, a pump, a vacuum, a motor, a gear, a sensor for guiding said circulator, and combinations thereof.

6. An apparatus according to claim 1, further comprising: means for agitating said particles inside said package.

7. An apparatus according to claim 6, wherein said agitating is at least one of the group consisting of rotating, shaking, vibrating, and combinations thereof.

8. An apparatus according to claim 1, further comprising: at least one of the group consisting of a sensor, a meter device, and combinations thereof for detecting at least one of the group consisting of a change in an external dimension of said package, inflation of said package, the airflow leakage rate of said package, and combinations thereof.

9. An apparatus according to claim 1, further comprising: at least one compressors for discharging at least a portion of said particles located inside said package from said package.

10. An apparatus according to claim 9, wherein said at least one compressor is coupled to said at least one clamping device.

11. An apparatus according to claim 1, further comprising:
at least one of the group consisting of a sample concentrating medium, a target selection sensing device, a predetermined sensitivity device, and combinations thereof.

12. An apparatus according to claim 1, further comprising:
at least one of the group consisting of a warning system, a device for sending alerts, a device for recording an output of said at least one biochemical detector, and combinations thereof.

13. An apparatus according to claim 1, wherein air located internal to said at least one of the group consisting of said airtight container and said approximately airtight container is mixed with a toxic gas to neutralize said biochemical hazard.

14. An apparatus according to claim 13, wherein said toxic gas is at least one of the group consisting of chlorine dioxide, methyl bromide, and combinations thereof.

15. An apparatus according to claim 1, wherein at least a portion of said at least one of the group consisting of said airtight container and said approximately airtight container is removable.

16. An apparatus according to claim 1, wherein said package is at least one of the group consisting of an envelope, an express mail package, and combinations thereof.

17. An apparatus according to claim 1, further comprising:
a conveyer system for delivering said package to said at least one of the group consisting of said airtight container and said approximately airtight container.

18. An apparatus according to claim 1, wherein said at least one circulator includes at least one probe inserted through a gap of said package.

19. An apparatus according to claim 1, wherein said at least one collector includes at least one vacuum for vacuuming said particles inside said envelope.

20. An apparatus according to claim 1, wherein collection of said particles from said inside of said package is facilitated by inflation of said package.

21. An apparatus according to claim 1, further comprising:
at least one cutting device for cutting said package.

22. An apparatus according to claim 21, wherein said at least one cutting device is at least one of the group consisting of a scissor, a syringe, and combinations thereof.

23. An apparatus according to claim 1, wherein said at least one biochemical detector is at least one of the group consisting of a laser analyzer, a photometer, an optical particle counter, a condensation particle counter, an optoelectronic sensor, and combinations thereof.

* * * * *